(12) United States Patent
Durfee (10) Patent No.: US 12,150,812 B2
(45) Date of Patent: Nov. 26, 2024

(54) SYSTEM AND METHOD FOR GENERATING VIRTUAL BLOOD VESSEL REPRESENTATIONS IN MIXED REALITY

(71) Applicant: Bard Access Systems, Inc., Salt Lake City, UT (US)

(72) Inventor: Tyler L. Durfee, Stansbury, UT (US)

(73) Assignee: Bard Access Systems, Inc., Salt Lake City, UT (US)

(*) Notice: Subject to any disclaimer, the term of this patent is extended or adjusted under 35 U.S.C. 154(b) by 0 days.

(21) Appl. No.: 17/397,486

(22) Filed: Aug. 9, 2021

(65) Prior Publication Data

US 2022/0039777 A1 Feb. 10, 2022

Related U.S. Application Data

(60) Provisional application No. 63/063,709, filed on Aug. 10, 2020.

(51) Int. Cl.
*A61B 8/00* (2006.01)
*A61B 8/08* (2006.01)
(Continued)

(52) U.S. Cl.
CPC ............ *A61B 8/463* (2013.01); *A61B 8/0891* (2013.01); *A61B 8/5207* (2013.01); *G06F 3/011* (2013.01); *A61B 2090/365* (2016.02)

(58) Field of Classification Search
CPC ..... A61B 8/463; A61B 8/0891; A61B 8/5207; A61B 8/523; A61B 8/461; A61B 8/4245; A61B 2090/365; G06F 3/011
See application file for complete search history.

(56) References Cited

U.S. PATENT DOCUMENTS 5,148,809 A 9/1992 Biegeleisen-Knight et al.
5,181,513 A 1/1993 Touboul et al.
(Continued)

FOREIGN PATENT DOCUMENTS

AU 2006201646 A1 11/2006
CN 114129137 B 9/2022
(Continued)

OTHER PUBLICATIONS

State, A., et al. (Aug. 1996). Technologies for augmented reality systems: Realizing ultrasound-guided needle biopsies. In Proceedings of the 23rd annual conference on computer graphics and interactive techniques (pp. 439-446) (Year: 1996).*
(Continued)

*Primary Examiner* — Christopher Koharski
*Assistant Examiner* — James F McDonald, III
(74) *Attorney, Agent, or Firm* — Rutan & Tucker LLP (57) ABSTRACT

A medical analytic system features an ultrasound probe communicatively coupled to a console, which includes a processor and a memory. The memory includes an alternative reality ("AR") anatomy representation logic, which can include representation logic with (i) visualization logic configured to capture information associated with multiple sub-images at different layers of an ultrasound image of an anatomical element, (ii) virtual slice positioning logic configured to position and orient each sub-image based on usage parameters during emission of the ultrasound signals from the ultrasound probe for capturing of the ultrasound image, (iii) virtual object assembly logic configured to assemble each of the sub-images to form a virtual representation of the anatomical element, and/or (iv) virtual object display logic configured to render the virtual representation of the anatomical element in an AR environment.

13 Claims, 7 Drawing Sheets

(51) Int. Cl.
  *G06F 3/01* (2006.01)
  *A61B 90/00* (2016.01)

(56) References Cited

U.S. PATENT DOCUMENTS

| | | | |
|---|---|---|---|
| 5,325,293 A | 6/1994 | Dorne | |
| 5,441,052 A | 8/1995 | Miyajima | |
| 5,549,554 A | 8/1996 | Miraki | |
| 5,573,529 A | 11/1996 | Haak et al. | |
| 5,775,322 A | 7/1998 | Silverstein et al. | |
| 5,879,297 A | 3/1999 | Haynor et al. | |
| 5,908,387 A | 6/1999 | LeFree et al. | |
| 5,967,984 A | 10/1999 | Chu et al. | |
| 5,970,119 A | 10/1999 | Hofmann | |
| 6,004,270 A | 12/1999 | Urbano et al. | |
| 6,019,724 A | 2/2000 | Gronningsaeter et al. | |
| 6,068,599 A | 5/2000 | Saito et al. | |
| 6,074,367 A | 6/2000 | Hubbell | |
| 6,129,668 A | 10/2000 | Haynor et al. | |
| 6,132,379 A | 10/2000 | Patacsil et al. | |
| 6,216,028 B1 | 4/2001 | Haynor et al. | |
| 6,233,476 B1 | 5/2001 | Strommer et al. | |
| 6,245,018 B1 | 6/2001 | Lee | |
| 6,263,230 B1 | 7/2001 | Haynor et al. | |
| 6,375,615 B1 | 4/2002 | Flaherty et al. | |
| 6,436,043 B2 | 8/2002 | Bonnefous | |
| 6,498,942 B1 | 12/2002 | Esenaliev et al. | |
| 6,503,205 B2 | 1/2003 | Manor et al. | |
| 6,508,769 B2 | 1/2003 | Bonnefous | |
| 6,511,458 B2 | 1/2003 | Milo et al. | |
| 6,524,249 B2 | 2/2003 | Moehring et al. | |
| 6,543,642 B1 | 4/2003 | Milliorn | |
| 6,554,771 B1 | 4/2003 | Buil et al. | |
| 6,592,520 B1 | 7/2003 | Peszynski et al. | |
| 6,592,565 B2 | 7/2003 | Twardowski | |
| 6,601,705 B2 | 8/2003 | Molina et al. | |
| 6,612,992 B1 | 9/2003 | Hossack et al. | |
| 6,613,002 B1 | 9/2003 | Clark et al. | |
| 6,623,431 B1 | 9/2003 | Sakuma et al. | |
| 6,641,538 B2 | 11/2003 | Nakaya et al. | |
| 6,647,135 B2 | 11/2003 | Bonnefous | |
| 6,687,386 B1 | 2/2004 | Ito et al. | |
| 6,749,569 B1 | 6/2004 | Pellegretti | |
| 6,754,608 B2 | 6/2004 | Svanerudh et al. | |
| 6,755,789 B2 | 6/2004 | Stringer et al. | |
| 6,840,379 B2 | 1/2005 | Franks-Farah et al. | |
| 6,857,196 B2 | 2/2005 | Dalrymple | |
| 6,979,294 B1 | 12/2005 | Selzer et al. | |
| 7,074,187 B2 | 7/2006 | Selzer et al. | |
| 7,244,234 B2 | 7/2007 | Ridley et al. | |
| 7,359,554 B2 | 4/2008 | Klingensmith et al. | |
| 7,534,209 B2 | 5/2009 | Abend et al. | |
| 7,599,730 B2 | 10/2009 | Hunter et al. | |
| 7,637,870 B2 | 12/2009 | Flaherty et al. | |
| 7,681,579 B2 | 3/2010 | Schwartz | |
| 7,691,061 B2 | 4/2010 | Hirota | |
| 7,699,779 B2 | 4/2010 | Sasaki et al. | |
| 7,720,520 B2 | 5/2010 | Willis | |
| 7,727,153 B2 | 6/2010 | Fritz et al. | |
| 7,734,326 B2 | 6/2010 | Pedain et al. | |
| 7,831,449 B2 | 11/2010 | Ying et al. | |
| 7,905,837 B2 | 3/2011 | Suzuki | |
| 7,925,327 B2 | 4/2011 | Weese | |
| 7,927,278 B2 | 4/2011 | Selzer et al. | |
| 8,014,848 B2 | 9/2011 | Birkenbach et al. | |
| 8,050,523 B2 | 11/2011 | Younge et al. | |
| 8,060,181 B2 | 11/2011 | Rodriguez Ponce et al. | |
| 8,068,581 B2 * | 11/2011 | Boese | A61B 5/06 378/98.12 |
| 8,075,488 B2 | 12/2011 | Burton | |
| 8,090,427 B2 | 1/2012 | Eck et al. | |
| 8,105,239 B2 | 1/2012 | Specht | |
| 8,172,754 B2 | 5/2012 | Watanabe et al. | |
| 8,175,368 B2 | 5/2012 | Sathyanarayana | |
| 8,200,313 B1 | 6/2012 | Rambod et al. | |
| 8,211,023 B2 | 7/2012 | Swan et al. | |
| 8,228,347 B2 | 7/2012 | Beasley et al. | |
| 8,298,147 B2 | 10/2012 | Huennekens et al. | |
| 8,303,505 B2 | 11/2012 | Webler et al. | |
| 8,323,202 B2 | 12/2012 | Roschak et al. | |
| 8,328,727 B2 | 12/2012 | Miele et al. | |
| 8,388,541 B2 | 3/2013 | Messerly et al. | |
| 8,409,103 B2 | 4/2013 | Grunwald et al. | |
| 8,449,465 B2 | 5/2013 | Nair et al. | |
| 8,553,954 B2 | 10/2013 | Saikia | |
| 8,556,815 B2 | 10/2013 | Pelissier et al. | |
| 8,585,600 B2 | 11/2013 | Liu et al. | |
| 8,622,913 B2 | 1/2014 | Dentinger et al. | |
| 8,706,457 B2 | 4/2014 | Hart et al. | |
| 8,727,988 B2 | 5/2014 | Flaherty et al. | |
| 8,734,357 B2 | 5/2014 | Taylor | |
| 8,744,211 B2 | 6/2014 | Owen | |
| 8,754,865 B2 | 6/2014 | Merritt et al. | |
| 8,764,663 B2 | 7/2014 | Smok et al. | |
| 8,781,194 B2 | 7/2014 | Malek et al. | |
| 8,781,555 B2 | 7/2014 | Burnside et al. | |
| 8,790,263 B2 | 7/2014 | Randall et al. | |
| 8,849,382 B2 | 9/2014 | Cox et al. | |
| 8,939,908 B2 | 1/2015 | Suzuki et al. | |
| 8,961,420 B2 | 2/2015 | Zhang | |
| 9,022,940 B2 | 5/2015 | Meier | |
| 9,138,290 B2 | 9/2015 | Hadjicostis | |
| 9,155,517 B2 | 10/2015 | Dunbar et al. | |
| 9,204,858 B2 | 12/2015 | Pelissier et al. | |
| 9,220,477 B2 | 12/2015 | Urabe et al. | |
| 9,257,220 B2 | 2/2016 | Nicholls et al. | |
| 9,295,447 B2 | 3/2016 | Shah | |
| 9,320,493 B2 | 4/2016 | Visveshwara | |
| 9,357,980 B2 | 6/2016 | Toji et al. | |
| 9,364,171 B2 | 6/2016 | Harris et al. | |
| 9,427,207 B2 | 8/2016 | Sheldon et al. | |
| 9,445,780 B2 | 9/2016 | Hossack et al. | |
| 9,456,766 B2 | 10/2016 | Cox et al. | |
| 9,456,804 B2 | 10/2016 | Tamada | |
| 9,459,087 B2 | 10/2016 | Dunbar et al. | |
| 9,468,413 B2 | 10/2016 | Hall et al. | |
| 9,492,097 B2 | 11/2016 | Wilkes et al. | |
| 9,521,961 B2 | 12/2016 | Silverstein et al. | |
| 9,554,716 B2 | 1/2017 | Burnside et al. | |
| 9,582,876 B2 | 2/2017 | Specht | |
| 9,597,008 B2 | 3/2017 | Henkel et al. | |
| 9,610,061 B2 | 4/2017 | Ebbini et al. | |
| 9,636,031 B2 | 5/2017 | Cox | |
| 9,649,037 B2 | 5/2017 | Lowe et al. | |
| 9,649,048 B2 | 5/2017 | Cox et al. | |
| 9,702,969 B2 | 7/2017 | Hope Simpson et al. | |
| 9,715,757 B2 | 7/2017 | Ng et al. | |
| 9,717,415 B2 * | 8/2017 | Cohen | G06T 7/0014 |
| 9,731,066 B2 | 8/2017 | Liu et al. | |
| 9,814,433 B2 | 11/2017 | Benishti et al. | |
| 9,814,531 B2 | 11/2017 | Yagi et al. | |
| 9,861,337 B2 | 1/2018 | Patwardhan et al. | |
| 9,895,138 B2 | 2/2018 | Sasaki | |
| 9,913,605 B2 | 3/2018 | Harris et al. | |
| 9,949,720 B2 | 4/2018 | Southard et al. | |
| 10,043,272 B2 | 8/2018 | Forzoni et al. | |
| 10,380,919 B2 | 8/2019 | Savitsky et al. | |
| 10,380,920 B2 | 8/2019 | Savitsky et al. | |
| 10,424,225 B2 | 9/2019 | Nataneli et al. | |
| 10,434,278 B2 | 10/2019 | Dunbar et al. | |
| 10,449,330 B2 | 10/2019 | Newman et al. | |
| 10,524,691 B2 | 1/2020 | Newman et al. | |
| 10,674,935 B2 | 6/2020 | Henkel et al. | |
| 10,751,509 B2 | 8/2020 | Misener | |
| 10,758,155 B2 | 9/2020 | Henkel et al. | |
| 10,765,343 B2 | 9/2020 | Henkel et al. | |
| 10,896,628 B2 | 1/2021 | Savitsky et al. | |
| 11,062,624 B2 | 7/2021 | Savitsky et al. | |
| 11,120,709 B2 | 9/2021 | Savitsky et al. | |
| 11,600,201 B1 | 3/2023 | Savitsky et al. | |
| 2002/0038088 A1 | 3/2002 | Imran et al. | |
| 2002/0148277 A1 | 10/2002 | Umeda | |
| 2003/0047126 A1 | 3/2003 | Tomaschko | |
| 2003/0060714 A1 | 3/2003 | Henderson et al. | |

(56) References Cited

U.S. PATENT DOCUMENTS

| | | |
|---|---|---|
| 2003/0073900 A1 | 4/2003 | Senarith et al. |
| 2003/0093001 A1 | 5/2003 | Martikainen |
| 2003/0106825 A1 | 6/2003 | Molina et al. |
| 2003/0120154 A1 | 6/2003 | Sauer et al. |
| 2004/0055925 A1 | 3/2004 | Franks-Farah et al. |
| 2005/0000975 A1 | 1/2005 | Carco et al. |
| 2005/0049504 A1 | 3/2005 | Lo et al. |
| 2005/0165299 A1 | 7/2005 | Kressy et al. |
| 2005/0251030 A1 | 11/2005 | Azar et al. |
| 2005/0267365 A1 | 12/2005 | Sokulin et al. |
| 2006/0013523 A1 | 1/2006 | Childlers et al. |
| 2006/0015039 A1 | 1/2006 | Cassidy et al. |
| 2006/0020204 A1 | 1/2006 | Serra et al. |
| 2006/0079781 A1 | 4/2006 | Germond-Rouet et al. |
| 2006/0184029 A1 | 8/2006 | Haim et al. |
| 2006/0210130 A1 | 9/2006 | Germond-Rouet et al. |
| 2007/0043341 A1 | 2/2007 | Anderson et al. |
| 2007/0049822 A1 | 3/2007 | Bunce et al. |
| 2007/0073155 A1 | 3/2007 | Park et al. |
| 2007/0199848 A1 | 8/2007 | Ellswood et al. |
| 2007/0239120 A1 | 10/2007 | Brock et al. |
| 2007/0249911 A1 | 10/2007 | Simon |
| 2008/0021322 A1 | 1/2008 | Stone et al. |
| 2008/0033293 A1 | 2/2008 | Beasley et al. |
| 2008/0033759 A1 | 2/2008 | Finlay |
| 2008/0051657 A1 | 2/2008 | Rold |
| 2008/0146915 A1 | 6/2008 | McMorrow |
| 2008/0177186 A1 | 7/2008 | Slater et al. |
| 2008/0221425 A1 | 9/2008 | Olson et al. |
| 2008/0294037 A1 | 11/2008 | Richter |
| 2008/0300491 A1 | 12/2008 | Bonde et al. |
| 2009/0012399 A1 | 1/2009 | Sunagawa et al. |
| 2009/0143672 A1 | 6/2009 | Harms et al. |
| 2009/0143684 A1 | 6/2009 | Cermak et al. |
| 2009/0156926 A1 | 6/2009 | Messerly et al. |
| 2009/0306509 A1 | 12/2009 | Pedersen et al. |
| 2010/0020926 A1* | 1/2010 | Boese ................ A61B 6/5241 |
| | | 359/9 |
| 2010/0106015 A1 | 4/2010 | Norris |
| 2010/0179428 A1 | 7/2010 | Pedersen et al. |
| 2010/0211026 A2 | 8/2010 | Sheetz et al. |
| 2010/0277305 A1 | 11/2010 | Garner et al. |
| 2010/0286515 A1 | 11/2010 | Gravenstein et al. |
| 2010/0312121 A1 | 12/2010 | Guan |
| 2011/0002518 A1 | 1/2011 | Ziv-Ari et al. |
| 2011/0071404 A1 | 3/2011 | Schmitt et al. |
| 2011/0295108 A1 | 12/2011 | Cox et al. |
| 2011/0313293 A1 | 12/2011 | Lindekugel et al. |
| 2012/0179038 A1 | 7/2012 | Meurer et al. |
| 2012/0197132 A1 | 8/2012 | O'Connor |
| 2012/0209121 A1 | 8/2012 | Boudier |
| 2012/0220865 A1 | 8/2012 | Brown et al. |
| 2012/0238875 A1 | 9/2012 | Savitsky et al. |
| 2012/0277576 A1 | 11/2012 | Lui |
| 2013/0041250 A1 | 2/2013 | Pelissier et al. |
| 2013/0102889 A1 | 4/2013 | Southard et al. |
| 2013/0131499 A1 | 5/2013 | Chan et al. |
| 2013/0131502 A1 | 5/2013 | Blaivas et al. |
| 2013/0150724 A1 | 6/2013 | Blaivas et al. |
| 2013/0188832 A1 | 7/2013 | Ma et al. |
| 2013/0218024 A1 | 8/2013 | Boctor et al. |
| 2013/0324840 A1 | 12/2013 | Zhongping et al. |
| 2014/0005530 A1 | 1/2014 | Liu et al. |
| 2014/0031690 A1* | 1/2014 | Toji .................... A61B 8/085 |
| | | 600/443 |
| 2014/0036091 A1 | 2/2014 | Zalev et al. |
| 2014/0073976 A1 | 3/2014 | Fonte et al. |
| 2014/0100440 A1 | 4/2014 | Cheline et al. |
| 2014/0155737 A1 | 6/2014 | Manzke et al. |
| 2014/0180098 A1 | 6/2014 | Flaherty et al. |
| 2014/0188133 A1 | 7/2014 | Misener |
| 2014/0188440 A1 | 7/2014 | Donhowe et al. |
| 2014/0257104 A1 | 9/2014 | Dunbar et al. |
| 2014/0276059 A1 | 9/2014 | Sheehan |
| 2014/0276081 A1 | 9/2014 | Tegels |
| 2014/0276085 A1 | 9/2014 | Miller |
| 2014/0276690 A1 | 9/2014 | Grace |
| 2014/0343431 A1 | 11/2014 | Vajinepalli et al. |
| 2015/0005738 A1 | 1/2015 | Blacker |
| 2015/0011887 A1 | 1/2015 | Ahn et al. |
| 2015/0065916 A1 | 3/2015 | Maguire et al. |
| 2015/0073279 A1 | 3/2015 | Cai et al. |
| 2015/0112200 A1 | 4/2015 | Oberg et al. |
| 2015/0209113 A1* | 7/2015 | Burkholz ............... A61B 5/743 |
| | | 600/417 |
| 2015/0209526 A1 | 7/2015 | Matsubara et al. |
| 2015/0294497 A1 | 10/2015 | Ng et al. |
| 2015/0297097 A1 | 10/2015 | Matsubara et al. |
| 2015/0327841 A1* | 11/2015 | Banjanin ............. A61B 8/4263 |
| | | 600/443 |
| 2015/0359991 A1 | 12/2015 | Dunbar et al. |
| 2016/0029995 A1 | 2/2016 | Navratil et al. |
| 2016/0029998 A1 | 2/2016 | Brister et al. |
| 2016/0058420 A1 | 3/2016 | Cinthio et al. |
| 2016/0100970 A1 | 4/2016 | Brister et al. |
| 2016/0101263 A1 | 4/2016 | Blumenkranz et al. |
| 2016/0113699 A1 | 4/2016 | Sverdlik et al. |
| 2016/0120607 A1 | 5/2016 | Sorotzkin et al. |
| 2016/0143622 A1 | 5/2016 | Xie et al. |
| 2016/0166232 A1 | 6/2016 | Merritt |
| 2016/0202053 A1 | 7/2016 | Walker et al. |
| 2016/0213398 A1 | 7/2016 | Liu |
| 2016/0278743 A1 | 9/2016 | Kawashima |
| 2016/0278869 A1 | 9/2016 | Grunwald |
| 2016/0296208 A1 | 10/2016 | Sethuraman et al. |
| 2016/0374644 A1 | 12/2016 | Mauldin, Jr. et al. |
| 2017/0079548 A1 | 3/2017 | Silverstein et al. |
| 2017/0086785 A1 | 3/2017 | Bjaerum |
| 2017/0100092 A1 | 4/2017 | Kruse et al. |
| 2017/0164923 A1 | 6/2017 | Matsumoto |
| 2017/0172424 A1 | 6/2017 | Eggers et al. |
| 2017/0188839 A1 | 7/2017 | Tashiro |
| 2017/0196535 A1 | 7/2017 | Arai et al. |
| 2017/0215842 A1 | 8/2017 | Ryu et al. |
| 2017/0259013 A1 | 9/2017 | Boyden et al. |
| 2017/0265840 A1 | 9/2017 | Bharat et al. |
| 2017/0303894 A1 | 10/2017 | Scully |
| 2017/0367678 A1 | 12/2017 | Sirtori et al. |
| 2018/0015256 A1 | 1/2018 | Southard et al. |
| 2018/0116723 A1 | 5/2018 | Hettrick et al. |
| 2018/0125450 A1 | 5/2018 | Blackbourne et al. |
| 2018/0161502 A1 | 6/2018 | Nanan et al. |
| 2018/0199914 A1 | 7/2018 | Ramachandran et al. |
| 2018/0214119 A1 | 8/2018 | Mehrmohammadi et al. |
| 2018/0225993 A1* | 8/2018 | Buras ..................... A61B 8/06 |
| 2018/0228465 A1 | 8/2018 | Southard et al. |
| 2018/0235576 A1 | 8/2018 | Brannan |
| 2018/0250078 A1 | 9/2018 | Shochat et al. |
| 2018/0272108 A1 | 9/2018 | Padilla et al. |
| 2018/0279996 A1 | 10/2018 | Cox et al. |
| 2018/0286287 A1 | 10/2018 | Razzaque |
| 2018/0310955 A1 | 11/2018 | Lindekugel et al. |
| 2018/0317881 A1* | 11/2018 | Astigarraga ......... A61B 8/0891 |
| 2018/0366035 A1 | 12/2018 | Dunbar et al. |
| 2019/0060014 A1 | 2/2019 | Hazelton et al. |
| 2019/0069923 A1 | 3/2019 | Wang |
| 2019/0076121 A1 | 3/2019 | Southard et al. |
| 2019/0088019 A1* | 3/2019 | Prevrhal ................. G06T 7/70 |
| 2019/0105017 A1 | 4/2019 | Hastings |
| 2019/0117190 A1* | 4/2019 | Djajadiningrat ...... G06T 19/006 |
| 2019/0223757 A1 | 7/2019 | Durfee |
| 2019/0239850 A1* | 8/2019 | Dalvin ................ A61B 8/4245 |
| 2019/0282324 A1* | 9/2019 | Freeman ........... A61M 16/0084 |
| 2019/0298457 A1 | 10/2019 | Bharat |
| 2019/0307516 A1 | 10/2019 | Schotzko et al. |
| 2019/0339525 A1* | 11/2019 | Yanof ..................... G06F 3/011 |
| 2019/0355278 A1* | 11/2019 | Sainsbury .............. A61B 34/30 |
| 2019/0365348 A1 | 12/2019 | Toume et al. |
| 2020/0041261 A1* | 2/2020 | Bernstein ................ F21V 7/005 |
| 2020/0069285 A1 | 3/2020 | Annangi et al. |
| 2020/0113540 A1 | 4/2020 | Gijsbers et al. |
| 2020/0129136 A1* | 4/2020 | Harding .................. G06F 3/011 |
| 2020/0188028 A1* | 6/2020 | Feiner .................... G06F 3/013 |
| 2020/0230391 A1* | 7/2020 | Burkholz ............... A61B 5/489 |

(56) References Cited

U.S. PATENT DOCUMENTS

| | | |
|---|---|---|
| 2021/0007710 A1 | 1/2021 | Douglas |
| 2021/0045716 A1 | 2/2021 | Shiran et al. |
| 2021/0166583 A1 | 6/2021 | Buras et al. |
| 2021/0307838 A1 | 10/2021 | Xia et al. |
| 2021/0353255 A1 | 11/2021 | Schneider et al. |
| 2021/0402144 A1 | 12/2021 | Messerly |
| 2022/0022969 A1 | 1/2022 | Misener |
| 2022/0031965 A1 | 2/2022 | Durfee |
| 2022/0160434 A1 | 5/2022 | Messerly et al. |
| 2022/0168050 A1 | 6/2022 | Sowards et al. |
| 2022/0172354 A1 | 6/2022 | Misener et al. |
| 2022/0211442 A1 | 7/2022 | McLaughlin et al. |
| 2023/0113291 A1 | 4/2023 | de Wild et al. |
| 2023/0240643 A1 | 8/2023 | Cermak et al. |
| 2023/0389893 A1 | 12/2023 | Misener et al. |
| 2024/0008929 A1 | 1/2024 | Misener et al. |
| 2024/0050061 A1 | 2/2024 | McLaughlin et al. |
| 2024/0058074 A1 | 2/2024 | Misener |
| 2024/0062678 A1 | 2/2024 | Sowards et al. |

FOREIGN PATENT DOCUMENTS

| | | | |
|---|---|---|---|
| EP | 0933063 A1 | 8/1999 | |
| EP | 1504713 A1 | 2/2005 | |
| EP | 1591074 B1 | 5/2008 | |
| EP | 3181083 A1 | 6/2017 | |
| EP | 3530221 A1 | 8/2019 | |
| JP | 2000271136 A | 10/2000 | |
| JP | 2014150928 A | 8/2014 | |
| JP | 2018175547 A | 11/2018 | |
| KR | 20180070878 A | 6/2018 | |
| KR | 20190013133 A | 2/2019 | |
| WO | 2013059714 A1 | 4/2013 | |
| WO | 2014/115150 A1 | 7/2014 | |
| WO | 2014174305 A2 | 10/2014 | |
| WO | 2015/017270 A1 | 2/2015 | |
| WO | 2017096487 A1 | 6/2017 | |
| WO | 2017214428 A1 | 12/2017 | |
| WO | 2018/026878 A1 | 2/2018 | |
| WO | 2018134726 A1 | 7/2018 | |
| WO | 2018206473 A1 | 11/2018 | |
| WO | 2019/232451 A1 | 12/2019 | |
| WO | 2020/002620 A1 | 1/2020 | |
| WO | 2020/016018 A1 | 1/2020 | |
| WO | 2019/232454 A9 | 2/2020 | |
| WO | 2020/044769 A1 | 3/2020 | |
| WO | WO-2020102665 A1 * | 5/2020 | ............. A61B 34/10 |
| WO | 2020/186198 A1 | 9/2020 | |
| WO | 2022263763 A1 | 12/2022 | |
| WO | 2023235435 A1 | 12/2023 | |
| WO | 2024010940 A1 | 1/2024 | |
| WO | 2024039608 A1 | 2/2024 | |
| WO | 2024039719 A1 | 2/2024 | |

OTHER PUBLICATIONS

PCT/US2021/045218 filed Aug. 9, 2021 International Search Report and Written Opinion dated Nov. 23, 2021.
Sebastian Vogt: "Real-Time Augmented Reality for Image-Guided Interventions", Oct. 5, 2009, XPO55354720, Retrieved from the Internet: URL: https://opus4.kobv.de/opus4-fau/frontdoor/deliver/index/docId/1235/file/SebastianVogtDissertation.pdf.
William F Garrett et al: "Real-time incremental visualization of dynamic ultrasound volumes using parallel BSP trees", Visualization '96. Proceedings, IEEE, NE, Oct. 27, 1996, pp. 235-ff, XPO58399771, ISBN: 978-0-89791-864-0 abstract, figures 1-7, pp. 236-240.
PCT/US12/61182 International Seach Report and Written Opinion dated Mar. 11, 2013.
PCT/US2021/049123 filed Sep. 3, 2021 International Search Report and Written Opinion dated Feb. 4, 2022.
PCT/US2021/049294 filed Sep. 7, 2021 International Search Report and Written Opinion dated Dec. 8, 2021.
PCT/US2021/049712 filed Sep. 9, 2021 International Search Report and Written Opinion dated Dec. 14, 2021.
PCT/US2021/052055 filed Sep. 24, 2021 International Search Report and Written Opinion dated Dec. 20, 2021.
U.S. Appl. No. 13/656,563, filed Oct. 19, 2012 Decision on Appeal dated Nov. 1, 2017.
U.S. Appl. No. 13/656,563, filed Oct. 19, 2012 Examiner's Answer dated Nov. 16, 2015.
U.S. Appl. No. 13/656,563, filed Oct. 19, 2012 Final Office Action dated Dec. 5, 2014.
U.S. Appl. No. 13/656,563, filed Oct. 19, 2012 Non-Final Office Action dated Jul. 18, 2014.
U.S. Appl. No. 15/650,474, filed Jul. 14, 2017 Final Office Action dated Jun. 2, 2020.
U.S. Appl. No. 15/650,474, filed Jul. 14, 2017 Non-Final Office Action dated Dec. 16, 2019.
U.S. Appl. No. 15/650,474, filed Jul. 14, 2017 Notice of Allowance dated Dec. 11, 2020.
U.S. Appl. No. 15/650,474, filed Jul. 14, 2017 Notice of Allowance dated Mar. 1, 2021.
U.S. Appl. No. 15/951,903, filed Apr. 12, 2018 Advisory Action dated Dec. 22, 2020.
U.S. Appl. No. 15/951,903, filed Apr. 12, 2018 Examiner's Answer dated Jun. 3, 2021.
U.S. Appl. No. 15/951,903, filed Apr. 12, 2018 Final Office Action dated Oct. 13, 2020.
U.S. Appl. No. 15/951,903, filed Apr. 12, 2018 Non-Final Office Action dated May 22, 2020.
U.S. Appl. No. 17/020,476, filed Sep. 14, 2020 Non-Final Office Action dated Feb. 9, 2022.
Ikhsan Mohammad et al: "Assistive technology for ultrasound-guided central venous catheter placement", Journal of Medical Ultrasonics, Japan Society of Ultrasonics in Medicine, Tokyo, JP, vol. 45, No. 1, Apr. 19, 2017, pp. 41-57, XPO36387340, ISSN: 1346-4523, DOI: 10.1007/S10396-017-0789-2 [retrieved on Apr. 19, 2017].
PCT/US2021/044419 filed Aug. 3, 2021 International Search Report and Written Opinion dated Nov. 19, 2021.
PCT/US2021/050973 filed Sep. 17, 2021 International Search Report and Written Opinion dated Nov. 7, 2022.
Lu Zhenyu et al "Recent advances in 5 robot-assisted echography combining perception control and cognition." Cognitive Computation and Systems the Institution of Engineering and Technology, Michael Faraday House, Six Hills Way, Stevenage Herts. SG1 2AY UK vol. 2 No. 3 Sep. 2, 2020 (Sep. 2, 2020).
Pagoulatos, N. et al. "New spatial localizer based on fiber optics with applications in 3D ultrasound imaging" Proceeding of Spie, vol. 3976 (Apr. 18, 2000; Apr. 18, 2000).
PCT/US2021/042369 filed Jul. 20, 2021 International Search Report and Written Opinion dated Oct. 25, 2021.
PCT/US2021/053018 filed Sep. 30, 2021 International Search Report and Written Opinion dated May 3, 2022.
PCT/US2021/055076 filed Oct. 14, 2021 International Search Report and Written Opinion dated Mar. 25, 2022.
U.S. Appl. No. 17/380,767, filed Jul. 20, 2021 Non-Final Office Action dated Mar. 6, 2023.
U.S. Appl. No. 17/380,767, filed Jul. 20, 2021 Restriction Requirement dated Dec. 15, 2022.
U.S. Appl. No. 17/393,283, filed Aug. 3, 2021 Non-Final Office Action dated Mar. 31, 2023.
U.S. Appl. No. 17/393,283, filed Aug. 3, 2021 Restriction Requirement dated Jan. 12, 2023.
U.S. Appl. No. 17/491,308, filed Sep. 30, 2021 Restriction Requirement dated Feb. 27, 2023.
U.S. Appl. No. 17/501,909, filed Oct. 14, 2021 Restriction Requirement dated Feb. 1, 2023.
Stolka, P.J., et al., (2014). Needle Guidance Using Handheld Stereo Vision and Projection for Ultrasound-Based Interventions. In: Galland, P., Hata, N., Barillot, C., Hornegger, J., Howe, R. (eds) Medical Image Computing and Computer-Assisted Intervention—MICCAI 2014. MICCAI 2014. (Year: 2014).
U.S. Appl. No. 17/491,308, filed Sep. 30, 2021 Final Office Action dated Aug. 29, 2023.

(56) References Cited

OTHER PUBLICATIONS

U.S. Appl. No. 17/491,308, filed Sep. 30, 2021 Non-Final Office Action dated Jun. 5, 2023.
U.S. Appl. No. 17/501,909, filed Oct. 14, 2021 Non-Final Office Action dated Jun. 6, 2023.
U.S. Appl. No. 17/832,389, filed Jun. 3, 2022 Restriction Requirement dated Jul. 13, 2023.
PCT/US2023/024067 filed May 31, 2023 International Search Report and Written Opinion dated Sep. 15, 2023.
PCT/US2023/027147 filed Jul. 7, 2023 International Search Report and Written Opinion dated Oct. 2, 2023.
PCT/US2023/030160 filed Aug. 14, 2023 International Search Report and Written Opinion dated Oct. 23, 2023.
PCT/US2023/030347 filed Aug. 16, 2023 International Search Report and Written Opinion dated Nov. 6, 2023.
Practical guide for safe central venous catheterization and management 2017 Journal of Anesthesia vol. 34 published online Nov. 30, 2019 pp. 167-186.
U.S. Appl. No. 17/380,767, filed Jul. 20, 2021 Notice of Allowance dated Aug. 31, 2023.
U.S. Appl. No. 17/393,283, filed Aug. 3, 2021 Final Office Action dated Oct. 16, 2023.
U.S. Appl. No. 17/491,308, filed Sep. 30, 2021 Board Decison dated Oct. 25, 2023.
U.S. Appl. No. 17/501,909, filed Oct. 14, 2021 Final Office Action dated Nov. 21, 2023.
U.S. Appl. No. 17/832,389, filed Jun. 3, 2022 Non-Final Office Action dated Oct. 6, 2023.
U.S. Appl. No. 17/861,031, filed Jul. 8, 2022 Non-Final Office Action dated Sep. 14, 2023.
U.S. Appl. No. 17/393,283, filed Aug. 3, 2021 Advisory Action dated Jan. 19, 2024.
U.S. Appl. No. 17/393,283, filed Aug. 3, 2021 Non-Final Office Action dated Feb. 29, 2024.
U.S. Appl. No. 17/478,754, filed Sep. 17, 2021 Restriction Requirement dated Jan. 22, 2024.
U.S. Appl. No. 17/491,308, filed Sep. 30, 2021 Non-Final Office Action dated Mar. 22, 2024.
U.S. Appl. No. 17/501,909, filed Oct. 14, 2021 Advisory Action dated Jan. 24, 2024.
U.S. Appl. No. 17/501,909, filed Oct. 14, 2021 Non-Final Office Action dated Mar. 21, 2024.
U.S. Appl. No. 17/832,389, filed Jun. 3, 2022 Advisory Action dated Apr. 4, 2024.
U.S. Appl. No. 17/832,389, filed Jun. 3, 2022 Final Office Action dated Jan. 25, 2024.
U.S. Appl. No. 17/832,389, filed Jun. 3, 2022 Notice of Allowance dated May 15, 2024.
U.S. Appl. No. 17/861,031, filed Jul. 8, 2022 Final Office Action dated Mar. 15, 2024.
U.S. Appl. No. 17/478,754, filed Sep. 17, 2021 Non-Final Office Action dated Jul. 1, 2024.
U.S. Appl. No. 17/491,308, filed Sep. 30, 2021 Notice of Allowance dated Jun. 27, 2024.
U.S. Appl. No. 17/501,909, filed Oct. 14, 2021 Final Office Action dated Aug. 5, 2024.
U.S. Appl. No. 17/861,031, filed Jul. 8, 2022 Advisory Action dated Jun. 7, 2024.
U.S. Appl. No. 17/861,031, filed Jul. 8, 2022 Notice of Allowance dated Jul. 3, 2024.
U.S. Appl. No. 18/385,101 filed Oct. 30, 2023 Notice of Allowance dated Aug. 20, 2024.

\* cited by examiner

SYSTEM AND METHOD FOR GENERATING VIRTUAL BLOOD VESSEL REPRESENTATIONS IN MIXED REALITY

PRIORITY

This application claims the benefit of priority to U.S. Provisional Patent Application No. 63/063,709, filed Aug. 10, 2020, which is incorporated by reference in its entirety into this application.

BACKGROUND

In the past, clinicians have relied on various guidance systems, such as ultrasound systems, for assistance in capturing and rendering an image of a vessel (e.g., vein, artery, etc.). However, conventional ultrasound systems only provide Doppler results to build an object, where such objects are visual images without any data characteristics associated with these images. Hence, diagnoses surrounding vessel health has been solely based on manual inspection of low-resolution images, which may lead to an unacceptable level of inaccurate diagnoses.

Hence, a system that leverages artificial intelligence to produce mixed reality and/or virtual reality images is needed.

SUMMARY

Disclosed herein is a medical analytic system including an ultrasound probe and a console communicatively coupled to the ultrasound probe. The console comprises an alternative reality ("AR") anatomy representation logic. The AR anatomy representation logic is configured to initiate a capture of information associated with multiple sub-images at different longitudinal positions of an ultrasound image of an anatomical element. The AR anatomy representation logic is also configured to position and orient each sub-image longitudinally based on usage parameters during emission of the ultrasound signals for capturing of the ultrasound image. Lastly, the AR anatomy representation logic is configured to assemble each of the sub-images to form a virtual representation of the anatomical element for rendering in an AR environment.

In some embodiments, the usage parameters include a speed in movement of the ultrasound probe during emission of the ultrasound signals for capturing of the ultrasound image.

In some embodiments, the usage parameters include a direction in movement of the ultrasound probe during emission of the ultrasound signals for capturing of the ultrasound image.

In some embodiments, the AR environment includes a mixed reality. The mixed reality includes the virtual representation of the anatomical element positioned over a real-world setting including a real depiction of a portion of a patient's body having the anatomical element.

In some embodiments, the anatomical element is a vessel within an arm or a leg of a patient.

In some embodiments, the console further includes a communication interface configured to provide a rendering of the virtual object to an AR headset.

Also disclosed herein is a medical analytic system including an ultrasound probe a console communicatively coupled to the ultrasound probe. The console includes a processor and a memory. The memory includes an AR anatomy representation logic including logic selected from the group consisting of visualization logic, virtual slice positioning logic, virtual object assembly logic, and virtual object display logic, provided at least two of the foregoing are selected. The visualization logic is configured to capture information associated with multiple sub-images at different layers of an ultrasound image of an anatomical element. The virtual slice positioning logic is configured to position and orient each sub-image based on usage parameters during emission of the ultrasound signals from the ultrasound probe for capturing of the ultrasound image. The virtual object assembly logic, when executed by the processor, is configured to assemble each of the sub-images to form a virtual representation of the anatomical element. The virtual object display logic, when executed by the processor, is configured to render the virtual representation of the anatomical element in an AR environment.

In some embodiments, the usage parameters include a speed in movement of the ultrasound probe during emission of the ultrasound signals for capturing of the ultrasound image.

In some embodiments, the usage parameters includes a direction in movement of the ultrasound probe during emission of the ultrasound signals for capturing of the ultrasound image.

In some embodiments, the AR environment includes a mixed reality. The mixed reality includes the virtual representation of the anatomical element positioned over a real-world setting including a real depiction of a portion of a patient's body having the anatomical element.

In some embodiments, the console further includes a communication interface to provide a rendering of the virtual object to an AR headset.

In some embodiments, the anatomical element is a vessel.

In some embodiments, the virtual object display logic is configured to render the virtual representation of the anatomical element as an overlay over an image or a series of images.

In some embodiments, the image includes the ultrasound image and the series of images including a video of a real-world setting.

In some embodiments, the visualization logic and the virtual slice positioning logic are implemented within the ultrasound probe. In addition, the virtual object assembly logic and the virtual object display logic are executed by the processor and implemented within the console.

In some embodiments, the visualization logic, the virtual slice positioning logic, the virtual object assembly logic, and the virtual object display logic are implemented as software executed by the processor within the console.

Also disclosed herein is a method including an information-capturing operation, a positioning-and-orienting operation, and an assembling operation. The information-capturing operation includes initiating a capture of information associated with multiple sub-images at different longitudinal positions of an ultrasound image of an anatomical element. The positioning-and-orienting operation includes positioning and orienting each sub-image of the multiple sub-images longitudinally based on usage parameters occurring during emission of ultrasound signals for capturing of the ultrasound image. The assembling operation includes assembling each of the sub-images to form a virtual representation of the anatomical element for rendering in an AR environment.

In some embodiments, the usage parameters include a speed in movement of the ultrasound probe during emission of the ultrasound signals for capturing of the ultrasound image. Alternatively, the usage parameters include a direction in movement of the ultrasound probe during emission of the ultrasound signals for capturing of the ultrasound image.

In some embodiments, the AR environment includes a mixed reality. The mixed reality includes the virtual representation of the anatomical element positioned over a real-world setting including a real depiction of a portion of a patient's body having the anatomical element.

In some embodiments, the anatomical element is a vessel within a body of a patient.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION

Reference will now be made to figures wherein like structures will be provided with like reference designations. It is understood that the drawings are diagrammatic and schematic representations of exemplary embodiments of the invention, and are neither limiting nor necessarily drawn to scale.

Regarding terms used herein, it should be understood the terms are for the purpose of describing some particular embodiments, and the terms do not limit the scope of the concepts provided herein. Ordinal numbers (e.g., first, second, third, etc.) are sometimes used to distinguish or identify different components or operations, and do not supply a serial or numerical limitation. For example, "first," "second," and "third" components or operations need not necessarily appear in that order, and the particular embodiments including such components or operations need not necessarily be limited to the three components or operations. Similarly, labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

The terms "logic" and "component" are representative of hardware and/or software that is configured to perform one or more functions. As hardware, logic (or component) may include circuitry having data processing and/or storage functionality. Examples of such circuitry may include, but are not limited or restricted to a processor, a programmable gate array, a microcontroller, an application specific integrated circuit, combinatorial circuitry, or the like. Alternatively, or in combination with the hardware circuitry described above, the logic (or component) may be software in the form of one or more software modules, which may be configured to operate as its counterpart circuitry. The software modules may include, for example, an executable application, a daemon application, an application programming interface ("API"), a subroutine, a function, a procedure, a routine, source code, or even one or more instructions. The software module(s) may be stored in any type of a suitable non-transitory storage medium, such as a programmable circuit, a semiconductor memory, non-persistent storage such as volatile memory (e.g., any type of random-access memory "RAM"), persistent storage such as non-volatile memory (e.g., read-only memory "ROM", power-backed RAM, flash memory, phase-change memory, etc.), a solid-state drive, hard disk drive, an optical disc drive, or a portable memory device.

With respect to "alternative reality," the term alternative reality may pertain to virtual reality, augmented reality, and mixed reality unless context suggests otherwise. "Virtual reality" includes virtual content in a virtual setting, which setting can be a fantasy or a real-world simulation. "Augmented reality" and "mixed reality" include virtual content in a real-world setting such as a real depiction of a portion of a patient's body including the anatomical element. Augmented reality includes the virtual content in the real-world setting, but the virtual content is not necessarily anchored in the real-world setting. For example, the virtual content can be information overlying the real-world setting. The information can change as the real-world setting changes due to time or environmental conditions in the real-world setting, or the information can change as a result of a consumer of the augmented reality moving through the real-world setting; however, the information remains overlying the real-world setting. Mixed reality includes the virtual content anchored in every dimension of the real-world setting. For example, the virtual content can be a virtual object anchored in the real-world setting. The virtual object can change as the real-world setting changes due to time or environmental conditions in the real-world setting, or the virtual object can change to accommodate the perspective of a consumer of the mixed reality as the consumer moves through the real-world setting. The virtual object can also change in accordance with any interactions with the consumer or another real-world or virtual agent. Unless the virtual object is moved to another location in the real-world setting by the consumer of the mixed reality, or some other real-world or virtual agent, the virtual object remains anchored in the real-world setting. Mixed reality does not exclude the foregoing information overlying the real-world setting described in reference to augmented reality.

In the following description, the terms "or" and "and/or" as used herein are to be interpreted as inclusive or meaning any one or any combination. As an example, "A, B or C" or "A, B and/or C" mean "any of the following: A; B; C; A and B; A and C; B and C; A, B and C." An exception to this definition will occur only when a combination of elements, components, functions, steps or acts are in some way inherently mutually exclusive.

Unless defined otherwise, all technical and scientific terms used herein have the same meaning as commonly understood by those of ordinary skill in the art.

Overview

Briefly summarized, embodiments disclosed herein are directed to a medical analytic system for representing a region of a patient's body for analysis. One of the embodiments may be directed to monitoring for the advancement of a medical component (e.g., needle, introducer, catheter, etc.) through sound waves (ultrasound) for example. As disclosed, the medical analytic system may include, in some embodiments, an ultrasound-imaging system and an AR headset for the analysis, where the ultrasound-imaging system includes AR anatomy representation logic.

More specifically, the ultrasound-imaging system includes an ultrasound probe and a console, which may be configured to include the AR anatomy representation logic or a portion thereof. The ultrasound probe is configured to emit ultrasound signals (sound waves) into a patient and receive echoed ultrasound signals (sound waves) from the patient by way of a piezoelectric sensor array or an array of capacitive micromachined ultrasonic transducers ("CMUTs"). According to one embodiment of the disclosure, the ultrasound probe may receive commands from the console to capture information associated with numerous "slices" of an anatomical element (e.g., a vessel, tissue, etc.) during ultrasound scanning; namely information associated with multiple (two or more) sub-images of an ultrasound image of the anatomical element where the sub-images are captured transverse to a longitudinal axis of the anatomical element. Each slice constitutes information associated with a two-dimensional ("2D") or three-dimensional ("3D") planar sub-image of the anatomical element, where multiple slices are overlaid to collectively reproduce a 3D representation of the anatomical element. Alternatively, as another embodiment of the disclosure, the ultrasound probe may include visualization logic that automatically captures ultrasound scanning information as to individual slices of an image associated with the anatomical element and provides the same to the console with results of the piezoelectric sensor array or the array of CMUTs.

The console features electronic circuitry including memory and a processor configured to transform the echoed ultrasound signals to produce ultrasound-image segments corresponding to anatomical structures of the patient. These ultrasound-image segments may be combined to form ultrasound frames for display. Additionally, according to one embodiment of the disclosure, the AR anatomy representation logic may be deployed as hardware, software, or a combination of hardware and software. For instance, when deployed as software, the AR anatomy representation logic may include visualization logic configured to issue commands to the ultrasound probe to capture multiple "slices" of the anatomical element image (e.g., a vessel, artery, etc.) during ultrasound scanning. The AR anatomy representation logic may further include virtual slice positioning logic to adjust the orientation and position each image slice, virtual object assembly logic to orderly assemble the imaged anatomical element, and virtual object display logic to render a virtual object along with the ultrasound imaged object.

More specifically, as the ultrasound probe scans and moves along an ultrasound imaging area to capture a vessel for example, the visualization logic controls the capturing of information associated with vertically-oriented portions (slices) of the ultrasound image (hereinafter, "slice images") and returns the slice images to the visual slice positioning logic. The virtual slice positioning logic is configured to determine the longitudinal orientation and positioning of each slice image based, at least in part, on the direction and speed of the ultrasound probe when in use, where such information is provided to the virtual object assembly logic. The virtual object assembly logic is configured to form the virtual object by longitudinally organizing the slice images and laterally overlaying the virtual object over the ultrasound image. For example, each visualization represented by a slice image would be positioned proximate to a neighboring slice image to construct, in a longitudinal direction, the virtual object such as a vessel virtual object.

Thereafter, the virtual object display logic is configured to display the collective slice images as the anatomical element in a virtual context (i.e., as a virtual object within a virtual reality view, a mixed reality view, or as a 3D model of the vessel).

The alternative-reality headset includes a display screen coupled to a headset frame having electronic circuitry including memory and a processor. The display screen may be configured such that a wearer of the alternative-reality headset can see the patient through the display screen. The display screen is configured to display objects of virtual anatomy over the patient corresponding to the ultrasound-image segments.

In some embodiments, the ultrasound probe is configured with a pulsed-wave Doppler imaging mode for emitting and receiving the ultrasound signals. The console is configured to capture ultrasound-imaging frames in accordance with the pulsed-wave Doppler imaging mode, combine the ultrasound-imaging frames together with an aggregation function, and segment the ultrasound-imaging frames or the aggregated ultrasound-imaging frames into the ultrasound-image segments with an image segmentation function.

In some embodiments, when the AR anatomy representation logic is activated, the console is configured to generate the virtual object as an aggregate of the ultrasound-image segments overlaid by a collection of virtualizations (image slices) by the virtual object assembly logic. The console is configured to send the objects of virtual anatomy to the alternative-reality headset for display over the patient.

Medical Analytic System Architecture

Figure 1:
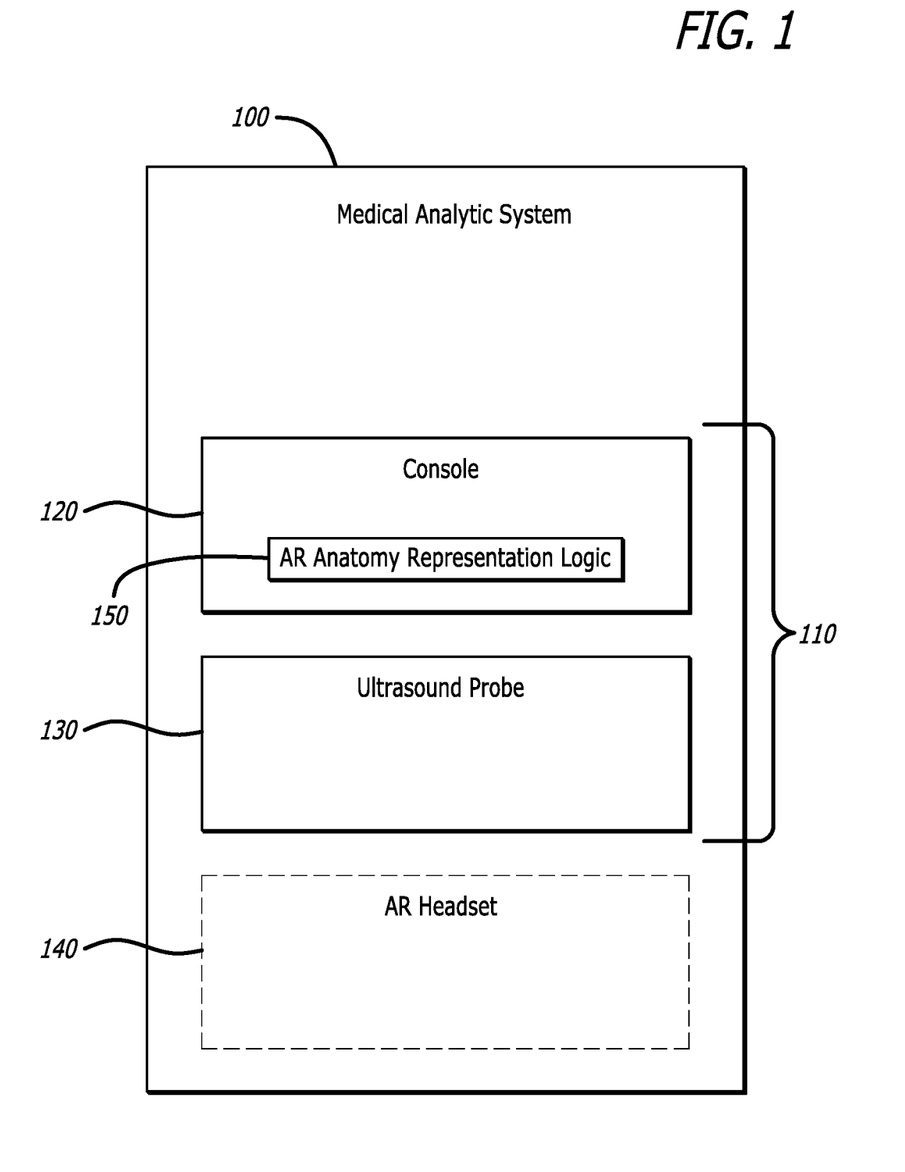
FIG. 1 is an exemplary block diagram of a medical analytic system with AR anatomy representation logic to generate a virtual object to overlay the ultrasound image.

Referring to FIG. 1, an illustrative embodiment of a medical analytic system 100 is shown. According to this embodiment of the disclosure, the medical analytic system 100 includes an ultrasound-imaging system 110 and an alternative-reality AR headset 140, The ultrasound-imaging system 110 includes a console 120 and an ultrasound probe 130, where the ultrasound-imaging system 110 features AR anatomy representation logic 150. The AR anatomy representation logic 150 may be configured to generate a virtual object that is presented in an AR environment such as a virtual reality, augmented reality or a mixed reality in which the virtual object overlays an image produced by the ultrasound-imaging system 110 (e.g., an ultrasound image) or a series of images (e.g., a video) associated with a real-world setting (e.g., video including a patient or a body part of the patient, a physical structure, etc.). The virtual object may be visible through the AR headset 140 or visible on a display of the console 120 without the AR headset 140. Alternatively, in lieu of the ultrasound-imaging system 110 as described herein, it is contemplated that a magnetic field imaging system may be deployed. It is contemplated that components and functions of the console 120 described in reference to the ultrasound-imaging system 110 should be understood to apply to the magnetic field imaging system or a similar system.

Notwithstanding the foregoing, in some embodiments of the medical analytic system 100, at least a portion of the functionality of the AR anatomy representation logic 150 may be deployed within the AR headset 140 in lieu of the console 120. Herein, the AR headset 140 or another component operating in cooperation with the AR headset 140 may serve as the console or performs the functions (e.g., processing) thereof.

Figure 2:
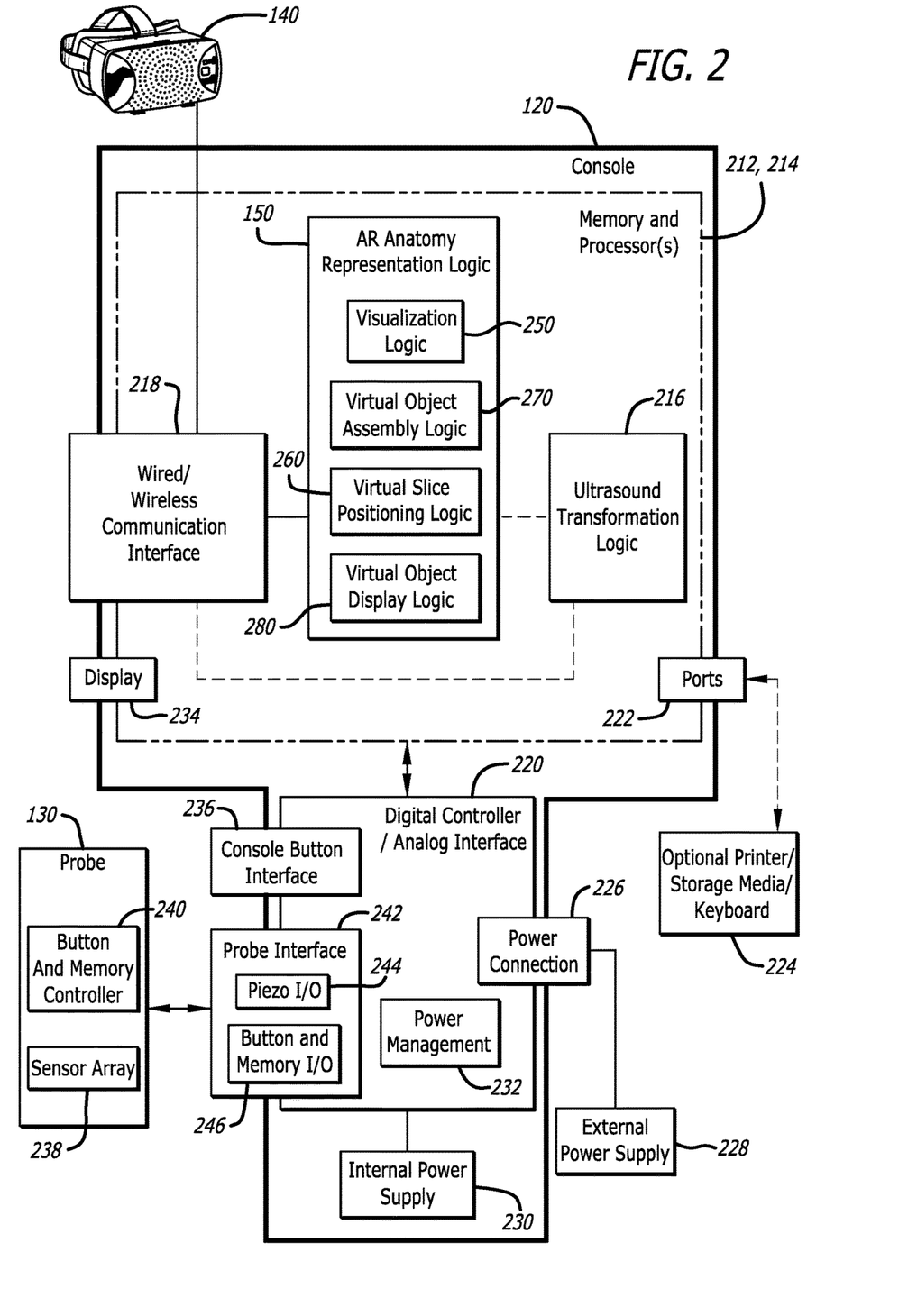
FIG. 2 is a first illustrative embodiment of the medical analytic system including the AR anatomy representation logic deployed therein.

More specifically, as shown in FIG. 2, a first illustrative embodiment of the medical analytic system 100, inclusive of the ultrasound probe 130 connected to the console 120 that includes the AR anatomy representation logic 150 is shown. Herein, the console 120 features electronic circuitry including memory 212 and one or more processors 214 configured to transform, in accordance with ultrasound transformation logic 216, echoed ultrasound signals to produce ultrasound frames and ultrasound-image segments therefrom corresponding to anatomical elements (e.g., structures) of the patient. The console 120 is configured to operate in a first mode to capture, in the memory 212, ultrasound-imaging frames (i.e., frame-by-frame ultrasound images) in accordance with a pulsed-wave Doppler imaging mode of the ultrasound probe 130, combine the ultrasound-imaging frames together with an aggregation function of the ultrasound transformation logic 216, and segment the ultrasound-imaging frames or the aggregated ultrasound-imaging frames into the ultrasound-image segments. In a second mode of operation, however, the console 120 may be configured to transform the ultrasound-image segments into an object of virtual anatomy (hereinafter, "virtual object") based on operations of certain components within the AR anatomy representation logic 150. The console 120 is configured to send the virtual object to the AR headset 140 for display over an image (e.g., ultrasound image) or a series of images (e.g., video of real-world setting) by way of a wired or wireless communications interface 218.

The console 120 includes a number of components of the medical analytic system 100, and the console 120 can take any form of a variety of forms to house the number of components. The one-or-more processors 214 and the memory 212 (e.g., non-volatile memory such as electrically erasable, programmable, read-only memory "EEPROM" or flash) of the console 120 are configured for controlling various functions of the medical analytic system 100 such as executing the AR anatomy representation logic 150 during operation of the medical analytic system 100. A digital controller or analog interface 220 is also included with the console 120, and the digital controller or analog interface 220 is in communication with the one-or-more processors 214 and other system components to govern interfacing between the ultrasound probe 130, the AR headset 140, as well as other system components.

The console 120 further includes ports 222 for connection with additional components such as optional components 224 including a printer, storage media, keyboard, etc. The ports 222 may be implemented as universal serial bus ("USB") ports, though other types of ports or a combination of port types can be used, as well as other interfaces or connections described herein. A power connection 226 may be included with the console 120 to enable operable connection to an external power supply 228. An internal power supply 230 (e.g., disposable or rechargeable battery) can also be employed, either with the external power supply 228 or exclusive of the external power supply 228. Power management circuitry 232 is included with the digital controller or analog interface 220 of the console 120 to regulate power use and distribution.

A display 234 can be, for example, a liquid crystal display ("LCD") integrated into the console 120 and used to display information to the clinician during a procedure. For example, the display 234 can be used to display an ultrasound image of a targeted internal body portion of the patient attained by the ultrasound probe 130. Additionally, or in the alternative, the display 234 can be used to display the virtual object positioned overlying the ultrasound image without the need of an AR headset 140. The virtual object would provide a more detailed, virtual representation of the internal anatomical element of the patient being imaged (e.g., vessel, tissue, etc.).

Alternatively, the display 234 can be separate from the console 120 instead of integrated into the console 120; however, such a display is different than that of the AR headset 140. The console 120 can further include a console button interface 236. In combination with control buttons on the ultrasound probe 130, the console button interface 236 can be used by a clinician to immediately call up a desired mode on the display 234 for use by the clinician. For example, two operating modes may include a first mode (e.g., ultrasound mode) and a second mode (e.g., AR enhanced mode), as stated above.

The ultrasound probe 130 is configured to emit ultrasound signals into the patient and receive the echoed ultrasound signals from the patient by way of a piezoelectric sensor array 238 or array of CMUTs. The ultrasound probe 130 can be configured with a continuous wave or a pulsed-wave imaging mode. For example, the ultrasound probe 130 can configured with the foregoing pulsed-wave Doppler imaging mode for emitting and receiving the ultrasound signals.

The ultrasound probe 130 further includes a button-and-memory controller 240 for governing operation of the ultrasound probe 130 and buttons thereof. The button-and-memory controller 240 can include non-volatile memory such as EEPROM. The button-and-memory controller 240 is in operable communication with an ultrasound probe interface 242 of the console 120, where the ultrasound probe interface 242 includes a piezoelectric input-output ("I/O") component 244 for interfacing with the piezoelectric sensor array 238 (or CMUT input-output ("I/O") component for interfacing with the array of CMUTs) of the ultrasound probe 130 and a button-and-memory I/O component 246 for interfacing with the button-and-memory controller 240 of the ultrasound probe 130. Hence, the operating mode of the ultrasound-imaging system 110 may be controlled at the ultrasound probe 130 (via the button-and-memory controller 240) and/or at the console 120 (via the console button interface 236).

As further illustrated in FIG. 2, the AR anatomy representation logic 150 includes visualization logic 250, virtual slice positioning logic 260, virtual object assembly logic 270, and virtual object display logic 280. Herein, according to one embodiment of the disclosure, the visualization logic 250 may be configured to produce visualizations (e.g., slice images of an anatomical element as captured by sound waves) by issuing commands to the ultrasound probe 130 to capture information associated with multiple "slices" of the anatomical element image during an ultrasound scanning session. Hence, information associated each frame (slice) of the ultrasound image may be captured at different prescribed periods of time during the ultrasound scanning session, where the slice images are generated from sound waves emitted by the ultrasound probe 130 at different longitudinal portions or positions of the ultrasound image as the wave propagate and return through the anatomical element. The information associated with an ultrasound frame may be used by the visualization logic 250 to generate a "virtual" slice image that, when aggregated, provide a virtual representation of the anatomical element captured by the ultrasound-imaging system 110 of FIG. 1.

Alternatively, according to another embodiment of the disclosure, the visualization logic 250 may be configured to produce slice images based on data associated with each ultrasound frame that is generated, where the aggregate of ultrasound frames constitutes the ultrasound image. From the data associated with each ultrasound frame, the visualization logic 250 is configured to generate a virtual representation of a portion of the anatomical element captured by that ultrasound image.

The virtual slice positioning logic 260 is configured to determine the position/orientation of each slice image generated by the visualization logic 250 based on, at least in part, the direction and speed of the ultrasound probe 130 when in use. For example, the speed in the movement of the ultrasound probe 130 may be relied upon to determine placement of a virtual slice image over the ultrasound image and along at least x-y axes of the virtual object. Similarly, the direction of the ultrasound probe 130 may be relied upon to determine placement of the virtual slice image over the ultrasound image along any or all of the x, y or z-axis.

The virtual object assembly logic 270 is communicatively coupled to the virtual slice positioning logic 260. Based on the positioning of the slice images, the virtual object assembly logic 270 is configured to generate a virtual object by longitudinally positioning each slice image at a determined location, where the virtual object is an aggregate of the positioned, slice images. As an illustrative example, each slice image is longitudinally organized adjacent to a neighboring slice image to construct the virtual object, such as a vessel virtual object for example.

The virtual object display logic 280 is communicatively coupled to the virtual object assembly logic 270. Herein, the virtual object display logic 280 is configured to display the aggregated, slice images as the virtual object that represent an anatomical element under analysis in a virtual context. The virtual context may include, but is not limited or restricted to a virtual reality view, a mixed reality view, or a 3D model of the anatomical element.

Figure 3A:
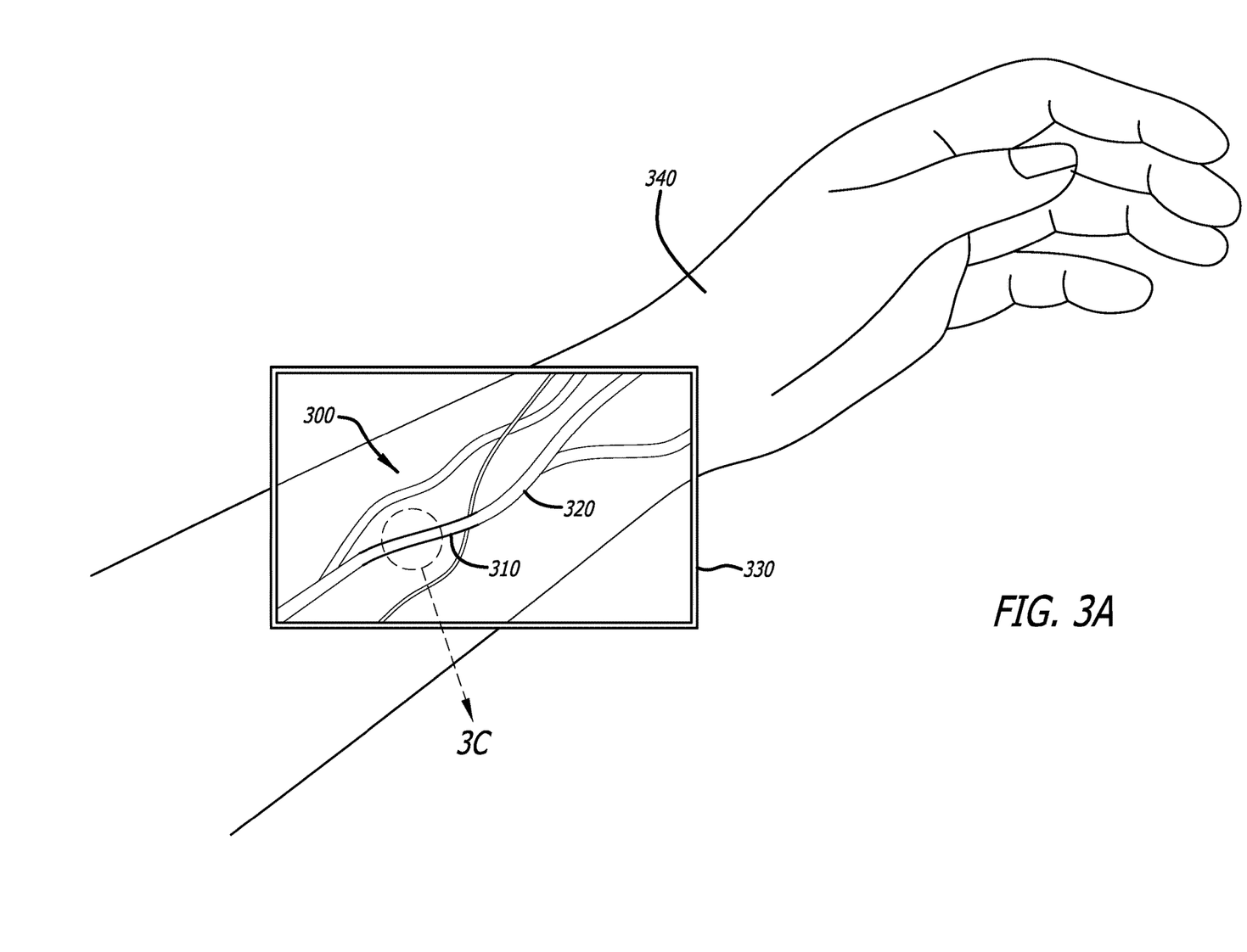
FIG. 3A is a perspective view of the virtual object overlaying the ultrasound image of the captured vessel.
Figure 3B:
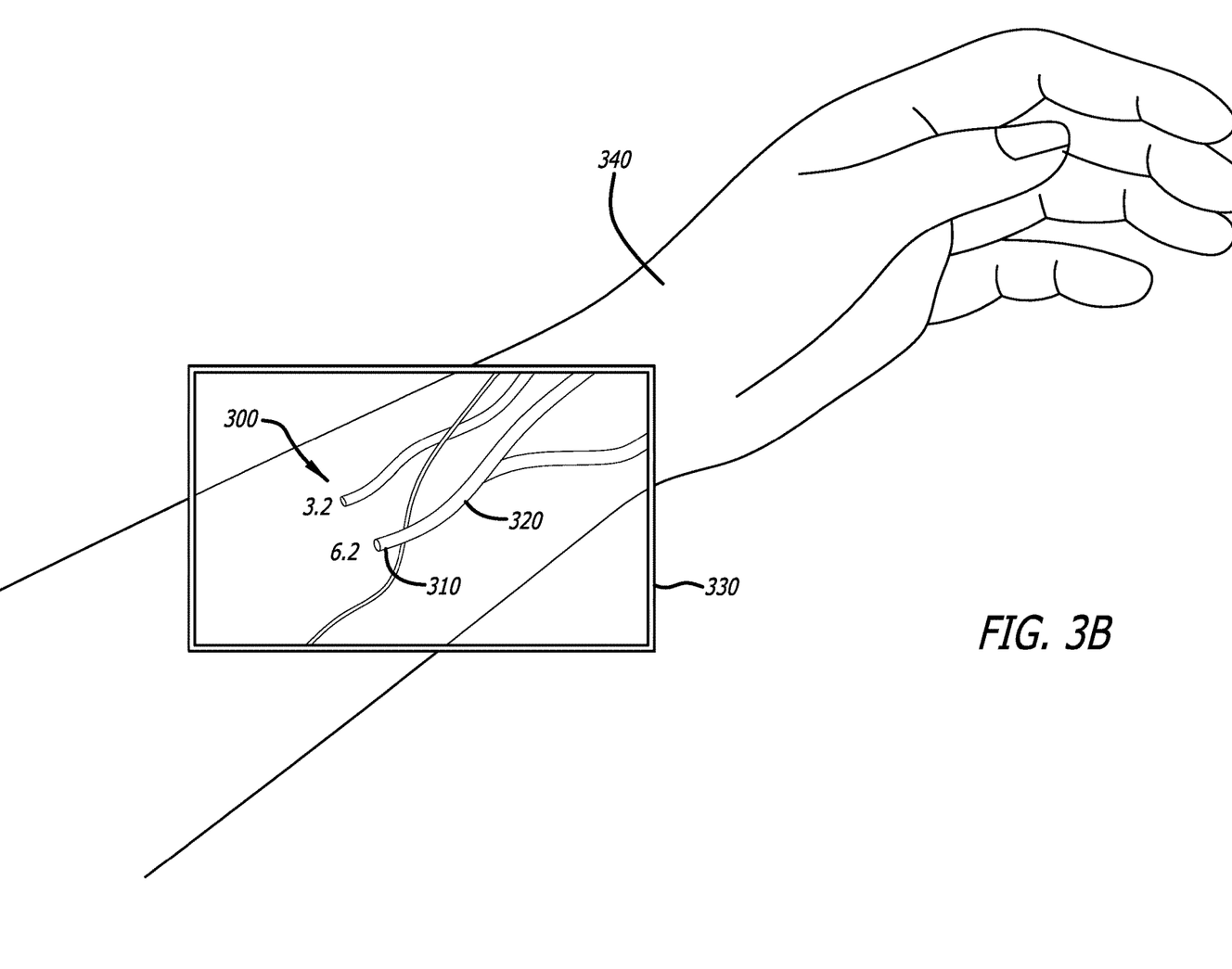
FIG. 3B is a perspective view of the virtual object overlaying the ultrasound image of the captured vessel.

Referring to FIGS. 3A and 3B, a perspective view of a virtual object 310 laterally overlaying an ultrasound image 300 of a captured vessel 320 is rendered on a display 330. Notably, FIG. 3B offers a different, deeper focus than that of FIG. 3A, wherein a cross section of the virtual object 310 and a nearby virtual object, for example, blood vessels, are displayed with their diameters. Information such as the diameters of blood vessels are useful for planning medical procedures such as catheterization. The display may be deployed as part of the console or as a separate display that may be positioned in an AR environment such as a mixed-reality setting in which the display 330 is position near a portion of a patient's arm 340 under diagnosis.

Figures 3C, 3D:
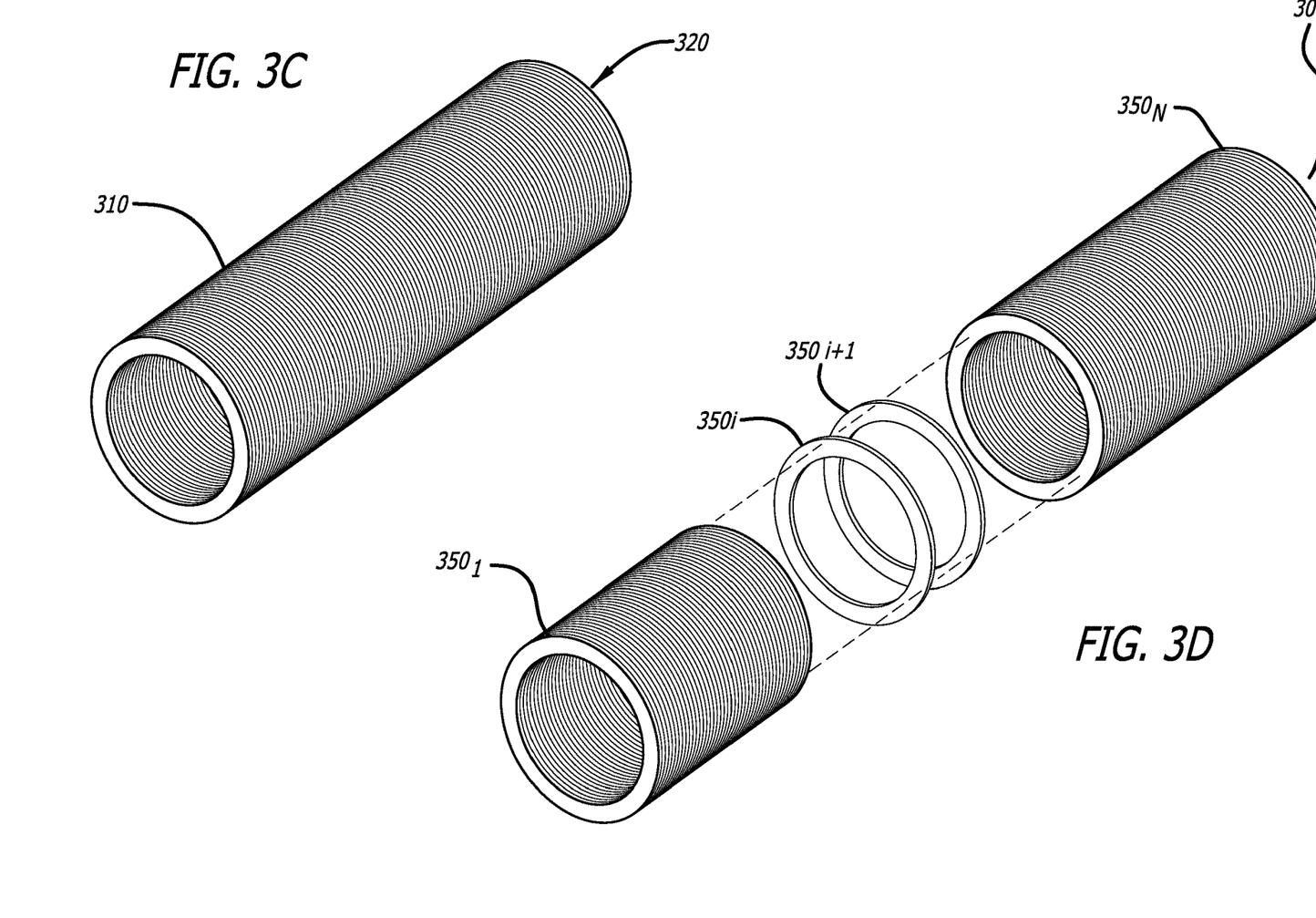
FIG. 3C is an illustrative embodiment of the virtual object of FIG. 3A.
FIG. 3D is a perspective view of multiple slice images of a vessel captured by the ultrasound probe of FIG. 2 to generate the virtual object of FIG. 3C.

As shown in FIGS. 3C and 3D, the virtual object 310 may be representative of a portion of the captured vessel 320, where multiple slice images $350_1$-$350_N$ ($N \geq 1$) of the ultrasound image 300 are captured (slices conducted traverse to a central axis of the image 300) using the ultrasound probe 130 of FIG. 2 to generate the virtual object 310. Herein, each of the slice images $350_1$-$350_N$ is generated by the visualization logic 250 of FIG. 2 based on information captured from a different sub-image of the ultrasound image 300 and positioned by the virtual slice positioning logic 260 of FIG. 2. Such positioning may be over a two-dimensional area (xz or yz-axes) while the virtual object assembly 270 is configured to generate the virtual object 310 by positioning the slice images $350_1$-$350_N$ at determined locations over a 3D area (xyz-axes), where the virtual object 310 is an aggregate of the positioned, slice images $350_1$-$350_N$, as shown in FIG. 3D.

Figure 4:
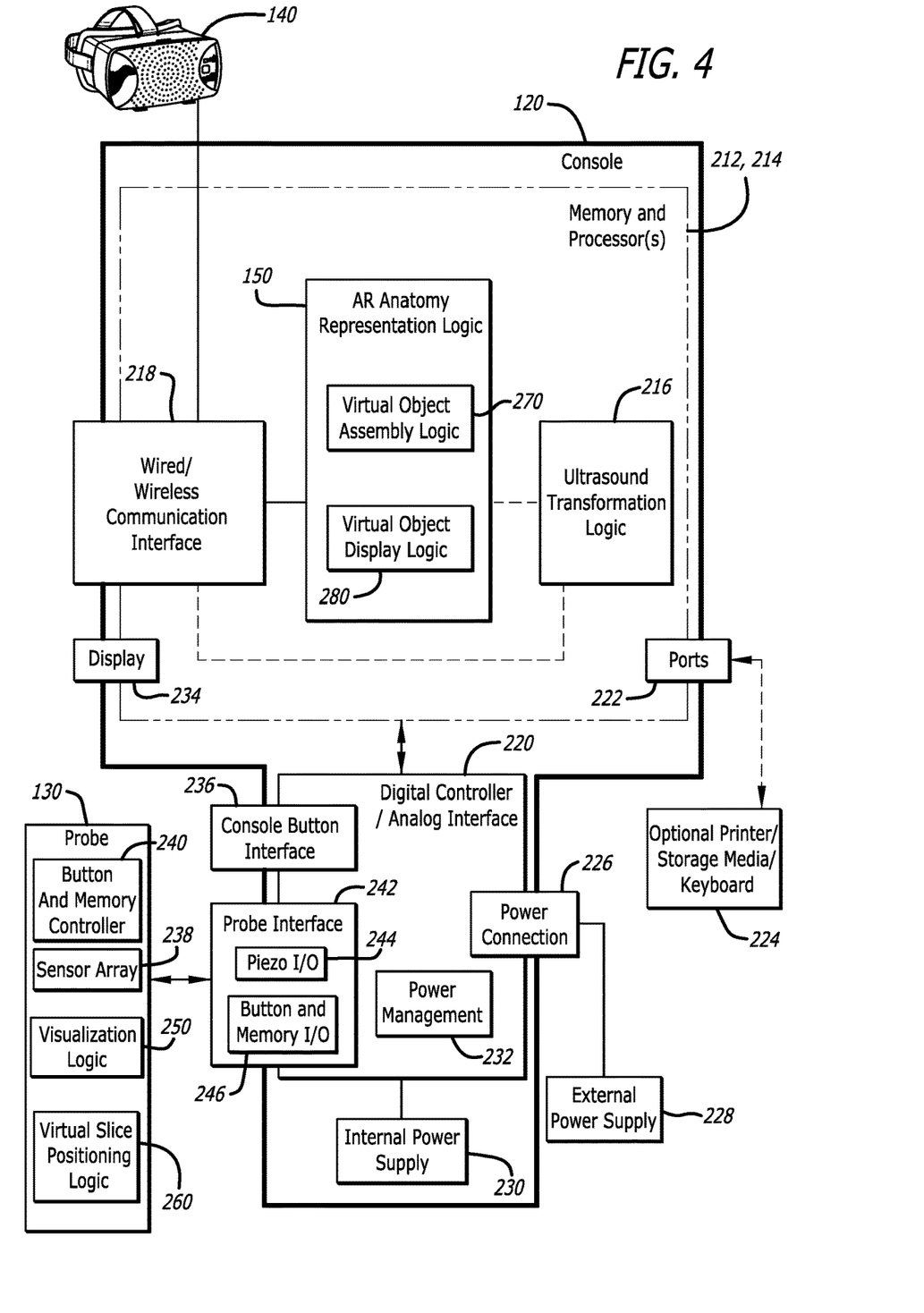
FIG. 4 is a second illustrative embodiment of the medical analytic system including the AR anatomy representation logic deployed within both the ultrasound probe and the console forming the medical analytic system.

Referring now to FIG. 4, a second illustrative embodiment of the medical analytic system 100 including the AR anatomy representation logic 150, where the logic is deployed within both the ultrasound probe 130 and the console 120 is shown. Herein, the medical analytic system 100 includes the console 120 and the ultrasound probe 130; however, for this embodiment of the disclosure, the visualization logic 250 and the virtual slice positioning logic 260 are deployed within the ultrasound probe 130 while the virtual assembly logic 270 and the virtual object display logic 280 are deployed within the console 120. The operability of this decentralized embodiment of the AR anatomy representation logic 150 is consistent with the operability of the AR anatomy representation logic 150 of FIG. 1.

Method

Figure 5:
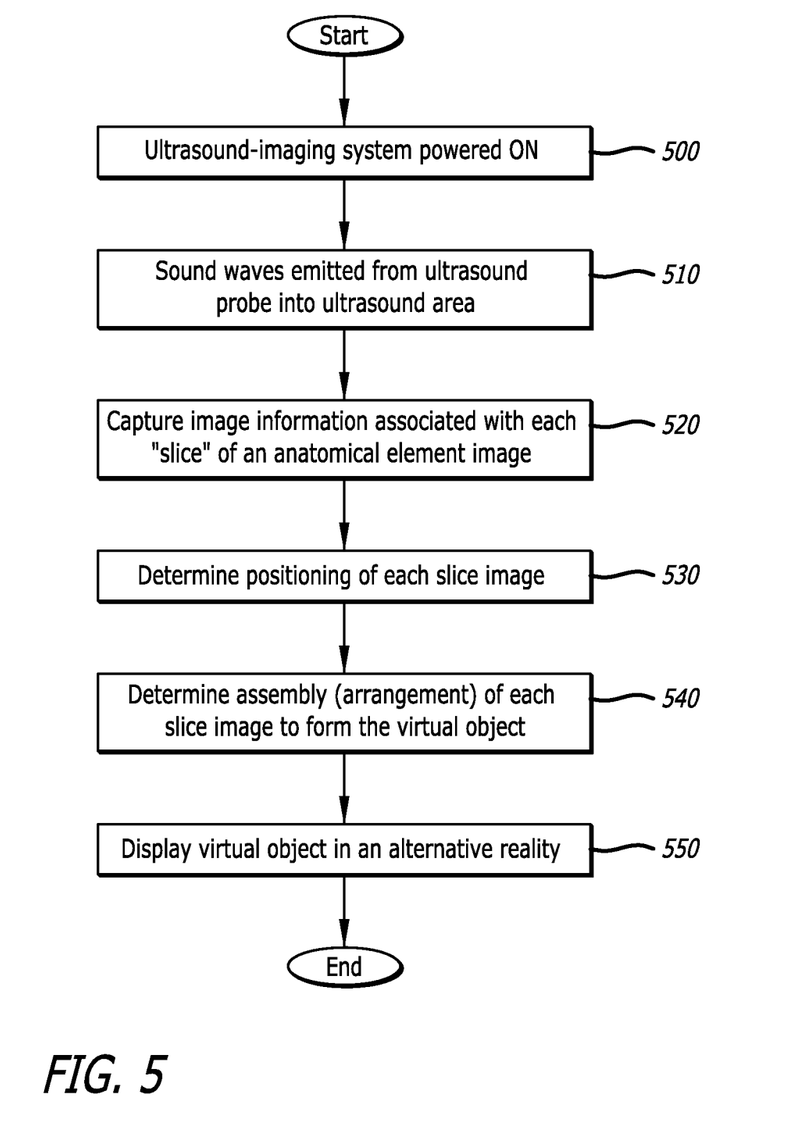
FIG. 5 is an exemplary method of operation conducted by the medical analytic system of FIG. 1.

Referring to FIG. 5, an exemplary method of operation conducted by the medical analytic system of FIGS. 1 and 4 is shown. According to one embodiment of the disclosure, the ultrasound-imaging system is powered on (operation 500) and sound waves are emitted from an ultrasound probe into an area of a patient's body (hereinafter, the "ultrasound area") to visualize an anatomical element (operation 510). Based on this visualization, the AR anatomy representation logic captures information associated with multiple "slices" of the anatomical element image during an ultrasound scanning session (operation 520). Each slice image may be associated with information pertaining to a sub-image or frame (layer) of the ultrasound image, and thus, each slice image is a virtualization of a portion of the ultrasound image of the anatomical element captured at a different moment in time.

After producing the multiple slices of the anatomical element image during an ultrasound scanning session, the AR anatomy representation logic, based on certain usage parameters associated with the ultrasound probe, determines the positioning of the slice image (operation 530) and the arrangement (assembly) of the slice images to produce the virtual object (operation 540). The positioning/assembly may be directed to lateral (xz-axis or yz-axis) arrangement of the slice images within the virtual representation of the anatomical element that corresponds to the virtual object. The usage parameters may include, but are not limited or restricted to speed and/or direction in movement of the ultrasound probe over the ultrasound area.

Thereafter, the AR anatomy representation logic is configured to display the virtual object in an alternative reality (operation 550), such as an overlay over the ultrasound image, where the virtual object may be more prevalent when viewed using an AR headset. However, the rendering of the virtual object on the display may be conducted so that the virtual object is visible without the AR headset.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A medical analytic system, comprising:
an ultrasound probe; and
a console communicatively coupled to the ultrasound probe, the console comprising a processor and a memory, wherein the memory includes an alternative reality ("AR") anatomy representation logic including:
(i) visualization logic configured to capture information associated with multiple sub-images at different layers of an ultrasound image of an anatomical element;
(ii) virtual slice positioning logic configured to position and orient each sub-image based on usage parameters during emission of ultrasound signals from the ultrasound probe for capturing the ultrasound image, the usage parameters including a speed in movement of the ultrasound probe over an ultrasound area;
(iii) virtual object assembly logic, when executed by the processor, configured to assemble each of the multiple sub-images to form a virtual representation of the anatomical element; and
(iv) virtual object display logic, when executed by the processor, configured to render the virtual representation of the anatomical element in an AR environment on a display screen of an AR headset.

2. The medical analytic system as defined in claim 1, wherein the speed in movement of the ultrasound probe over the ultrasound area determines placement of a virtual slice image over the ultrasound image.

3. The medical analytic system as defined in claim 1, wherein the AR environment includes a mixed reality in which the virtual representation of the anatomical element is positioned over a real-world setting being a real depiction of a portion of a patient's body including the anatomical element.

4. The medical analytic system as defined in claim 1, wherein the console further comprises a communication interface to provide a rendering of the virtual representation to the AR headset.

5. The medical analytic system as defined in claim 1, wherein the anatomical element is a vessel.

6. The medical analytic system as defined in claim 1, wherein the virtual object display logic is configured to render the virtual representation of the anatomical element as an overlay over one or more ultrasound images.

7. The medical analytic system as defined in claim 6, wherein the virtual object display logic is configured to render the overlay over a series of ultrasound images including a video of a real-world setting.

8. The medical analytic system as defined in claim 1, wherein the visualization logic and the virtual slice positioning logic are implemented within the ultrasound probe and the virtual object assembly logic and the virtual object display logic are executed by the processor and implemented within the console.

9. The medical analytic system as defined in claim 1, wherein the visualization logic, the virtual slice positioning logic, the virtual object assembly logic and the virtual object display logic are implemented as software executed by the processor within the console.

10. A method comprising:
initiating a capture of information associated with multiple sub-images at different longitudinal positions of an ultrasound image of an anatomical element;
positioning and orienting each sub-image of the multiple sub-images longitudinally based on usage parameters occurring during emission of ultrasound signals for capturing the ultrasound image, the usage parameters including a speed in movement of an ultrasound probe over an ultrasound area;
assembling each of the multiple sub-images to form a virtual representation of the anatomical element for rendering in an alternative reality ("AR") environment; and
rendering the virtual representation of the anatomical element in the AR environment on a display screen of an AR headset.

11. The method as defined in claim 10, wherein the usage parameters include a direction in movement of the ultrasound probe during emission of the ultrasound signals for capturing the ultrasound image.

12. The method as defined in claim 10, wherein the AR environment includes a mixed reality in which the virtual representation of the anatomical element is positioned over a real-world setting being a real depiction of a portion of a patient's body including the anatomical element, and the anatomical element is a vessel within a body of a patient.

13. The medical analytic system as defined in claim 5, wherein the virtual representation of the anatomical element is displayed with a diameter, the diameter being useful for medical procedures such as catheterization.

* * * * *